US00PP25385P2

(12) United States Plant Patent
Sakazaki

(10) Patent No.: US PP25,385 P2
(45) Date of Patent: Mar. 24, 2015

(54) ***CALIBRACHOA* PLANT NAMED 'USCAL 12202'**

(50) Latin Name: ***Calibrachoa* sp.**
Varietal Denomination: USCAL12202

(71) Applicant: Ushio Sakazaki, Hikone (JP)

(72) Inventor: Ushio Sakazaki, Hikone (JP)

(73) Assignee: Plant 21 LLC, Bonsall, CA (US)

( * ) Notice: Subject to any disclaimer, the term of this patent is extended or adjusted under 35 U.S.C. 154(b) by 50 days.

(21) Appl. No.: 13/986,834

(22) Filed: Jun. 10, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — C. A. Whealy

(57) ABSTRACT

A new and distinct cultivar of *Calibrachoa* plant named 'USCAL12202', characterized by its upright, outwardly spreading to trailing and mounding plant habit; freely branching habit; dense and bushy appearance; freely flowering habit; pale golden yellow and brown bi-colored flowers; and good garden performance.

1 Drawing Sheet

Botanical designation: *Calibrachoa* sp.
Cultivar denomination: 'USCAL12202'.

BACKGROUND OF THE INVENTION

The present invention relates to a new and distinct cultivar of *Calibrachoa* plant, botanically known as *Calibrachoa* sp. and hereinafter referred to by the name 'USCAL12202'.

The new *Calibrachoa* plant is a product of a planned breeding program conducted by the Inventor in Higashiomi, Shiga, Japan and Bonsall, Calif. The objective of the breeding program is to create new uniform and freely-branching *Calibrachoa* plants with unique and attractive flower coloration and good garden performance.

The new *Calibrachoa* plant originated from a cross-pollination made by the Inventor on May 11, 2010 in Higashiomi, Shiga, Japan of a proprietary seedling selection of *Calibrachoa* sp. identified as code name 10CJ69-07, not patented, as the female, or seed, parent with a proprietary seedling selection of *Calibrachoa* sp. identified as code name 10CJ20, not patented, as the male, or pollen, parent. The new *Calibrachoa* plant was discovered and selected by the Inventor as a single flowering plant within the progeny of the stated cross-pollination in a controlled environment in Bonsall, Calif. on May 13, 2011.

Asexual reproduction of the new *Calibrachoa* plant by terminal cuttings in a controlled environment in Bonsall, Calif. since May 14, 2011 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL12202'. These characteristics in combination distinguish 'USCAL12202' as a new and distinct *Calibrachoa* plant:

1. Upright, outwardly spreading to trailing and mounding plant habit.
2. Freely branching habit; dense and bushy appearance.
3. Freely flowering habit.
4. Pale golden yellow and brown bi-colored flowers.
5. Good garden performance.

The new *Calibrachoa* plant can be compared to plants of the female parent selection. Plants of the new *Calibrachoa* differ primarily from plants of the female parent selection in the following characteristics:

1. Plants of the new *Calibrachoa* are more mounding than and not as spreading as plants of the female parent selection.
2. Plants of the new *Calibrachoa* and the female parent selection differ in flower color as plants of the female parent selection have light brownish blue-colored flowers.

The new *Calibrachoa* plant can be compared to plants of the male parent selection. Plants of the new *Calibrachoa* differ primarily from plants of the male parent selection in the following characteristics:

1. Plants of the new *Calibrachoa* are more mounding than and not as upright as plants of the male parent selection.
2. Plants of the new *Calibrachoa* and the male parent selection differ in flower color as plants of the male parent selection have creamy yellow-colored flowers.

Plants of the new *Calibrachoa* can be compared to plants of the *Calibrachoa* sp. 'USCA66501', disclosed in U.S. Plant Pat. No. 22,942. In side-by-side comparisons conducted in Bonsall, Calif., plants of the new *Calibrachoa* differed primarily from plants of 'USCAL66501' in flower color as plants of 'USCAL66501' had coral red-colored flowers with greyed purple-colored centers.

Plants of the new *Calibrachoa* can be compared to plants of the *Calibrachoa* sp. 'USCALI413-8', disclosed in U.S. Plant Pat. No. 19,843. In side-by-side comparisons conducted in Bonsall, Calif., plants of the new *Calibrachoa* differed primarily from plants of 'USCALI413-8' in flower color as plants of 'USCALI413-8' had orange-colored flowers with red-colored centers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL12202' grown in a container.

The photograph at the top of the sheet is a close-up view of a typical flowering plant of 'USCAL12202'.

DETAILED BOTANICAL DESCRIPTION

The aforementioned photographs and following observations, measurements and values describe plants grown during the spring in 15.25-cm containers in a polyethylene-covered greenhouse in Bonsall, Calif. During the production of the plants, day temperatures averaged 24° C. and night temperatures averaged 18° C. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL12202'.

Parentage:

*Female, or seed, parent*.—Proprietary seedling selection of *Calibrachoa* sp. identified as code name 10CJ69-07, not patented.

*Male, or pollen, parent*.—Proprietary seedling selection of *Calibrachoa* sp. identified as code number 10CJ20, not patented.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 16° C. to 29° C.

*Time to produce a rooted plant, winter*.—About 25 days at temperatures ranging from 16° C. to 21° C.

*Root description*.—Medium in thickness, fibrous; white in color.

*Rooting habit*.—Freely branching; medium density.

Plant description:

*Plant and growth habit*.—Upright, outwardly spreading to trailing and mounding plant habit; freely branching habit with about eight primary lateral branches each with multiple secondary branches; pinching enhances branching; dense and bushy appearance; vigorous growth habit.

*Plant height*.—About 14.2 cm.

*Plant diameter*.—About 32 cm.

Lateral branch description:

*Length*.—About 21.5 cm.

*Diameter*.—About 2 mm.

*Internode length*.—About 1.8 cm.

*Strength*.—Strong.

*Aspect*.—Initially upright to outwardly spreading to trailing.

*Texture*.—Pubescent.

*Color*.—Close to 146B.

Foliage description:

*Arrangement*.—Before flowering, alternate; after flowering, opposite; leaves simple.

*Length*.—About 3.8 cm.

*Width*.—About 1.4 cm.

*Shape*.—Elliptical.

*Apex*.—Rounded.

*Base*.—Attenuate.

*Margin*.—Entire.

*Texture, upper and lower surfaces*.—Pubescent; minute.

*Venation pattern*.—Pinnate; arcuate to reticulate.

*Color*.—Developing leaves, upper surface: Close to 146A. Developing leaves, lower surface: Close to 147B. Fully expanded leaves, upper surface: Close to 137A; venation, close to 147B. Fully expanded leaves, lower surface: Close to 147B; venation, close to 147C.

*Petiole*.—Length: About 5 mm. Diameter: About 1.5 mm. Texture, upper and lower surfaces: Scattered pubescence. Color, upper and lower surfaces: Close to 147C.

Flower description:

*Flower type and flowering habit*.—Single salverform flowers arising from leaf axils; freely flowering habit with usually about eight to ten flowers developing per lateral branch and about 142 flowers developing per plant; flowers face upright to outwardly.

*Fragrance*.—None detected.

*Natural flowering season*.—Plants of the new *Calibrachoa* begin flowering about seven weeks after planting; plants flower continuously from spring though the summer until autumn in Southern California.

*Flower longevity*.—Individual flowers last about four to five days on the plant; flowers persistent.

*Flower buds*.—Length: About 2.8 cm. Diameter: About 1 cm. Shape: Elongated oblong. Color: Close to 162D.

*Flower diameter*.—About 3.8 cm.

*Flower length* (*height*).—About 2.7 cm.

*Flower throat diameter*.—About 5 mm by 7 mm.

*Flower tube length*.—About 2 cm.

*Flower tube diameter, base*.—About 2 mm.

*Corolla*.—Arrangement: Five fused petals opening into a flared trumpet. Petal lobe length (from throat): About 1.5 cm. Petal lobe width: About 1.6 cm. Petal shape: Fan-shaped. Petal apex: Rounded. Petal margin: Entire. Petal texture, upper surface: Smooth, glabrous; velvety. Petal texture, lower surface: Scattered pubescence; minute and mostly along the veins. Throat texture: Smooth, glabrous. Tube texture: Pubescent; minute. Color: Petal lobe, when opening, upper surface: Close to 162C; towards the center, close to 200B. Petal lobe, when opening, lower surface: Close to 160D. Petal lobe, fully opened, upper surface: Close to 162B to 162C; towards the throat, close to 200A to 200B; venation, close to 200B; color does not fade with development. Petal lobe, fully opened, lower surface: Close to 162D tinged with close to 187A to 187B; venation, close to 200A. Throat: Close to 7D; venation, close to 199A. Tube: Close to 2D; venation, close to 200B.

*Calyx*.—Arrangement: One star-shaped calyx tube with five sepals fused towards the base and arranged in a single whorl. Sepal length: About 1.7 cm. Sepal width: About 3 mm. Sepal shape: Oblanceolate. Sepal apex: Broadly acute to almost round. Sepal margin: Entire. Sepal texture, upper surface: Pubescent; scattered and minute. Sepal texture, lower surface: Pubescent; minute. Sepal color, upper surface: Close to N137A. Sepal color, lower surface: Close to N137B.

*Peduncles*.—Length: About 2.2 cm. Diameter: About 1 mm. Angle: About 45° from stem axis. Strength: Moderately strong. Texture: Pubescent; minute. Color: Close to 146B.

*Reproductive organs*.—Stamens: Quantity: Five per flower. Filament length: About 8 mm. Filament color: Close to 145D. Anther length: About 1 mm. Anther shape: Oval. Anther color: Close to 11A. Pollen amount: Scarce. Pollen color: Close to 8A. Pistils: Quantity: One per flower. Pistil length: About 9 mm. Style length: About 7 mm. Style color: Close to 145C. Stigma shape: Round. Stigma color: Close to 137B. Ovary color: Close to 145B. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL12202' as illustrated and described.

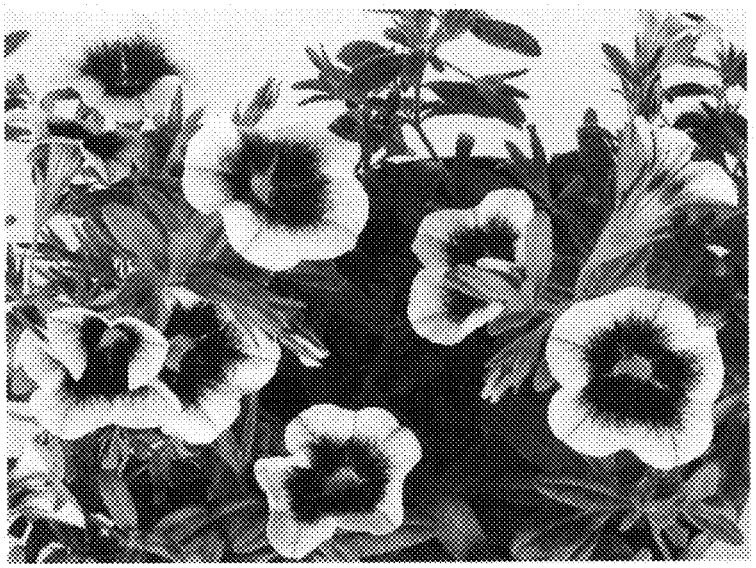
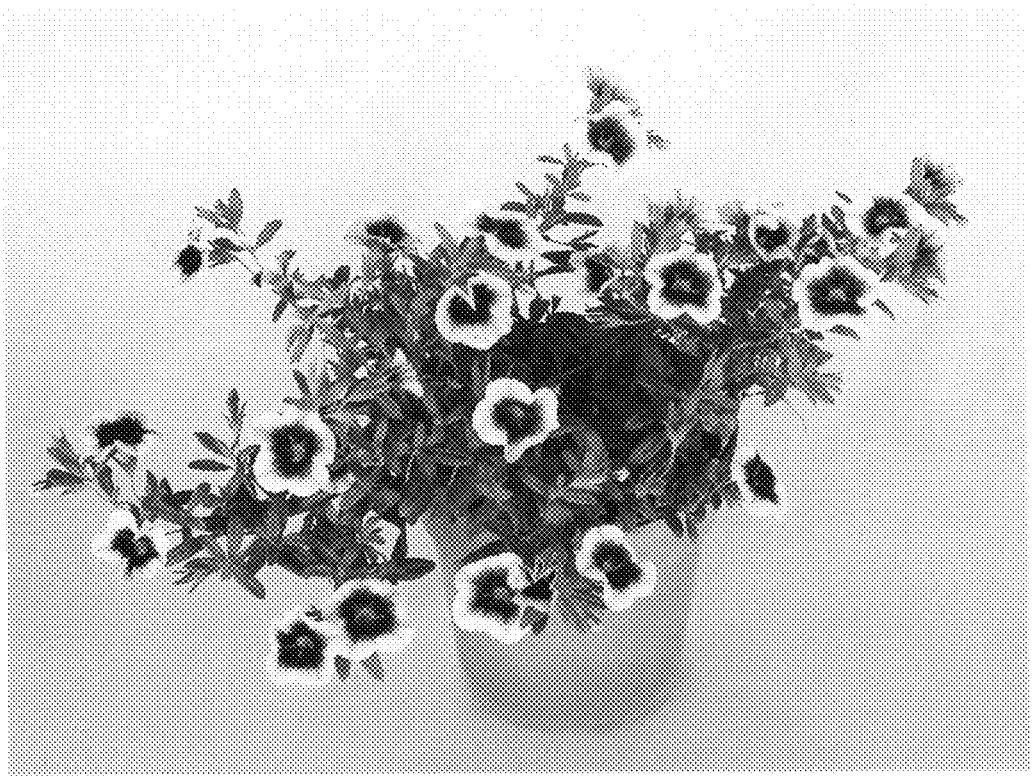

* * * * *